United States Patent
Dunkley et al.

(10) Patent No.: US 8,399,009 B2
(45) Date of Patent: Mar. 19, 2013

(54) BIOCERAMIC AND BIOPOLYMER COMPOSITE

(75) Inventors: Ian Robert Dunkley, Kingston (CA); Reginald William Smith, Kingston (CA)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 12/955,109

(22) Filed: Nov. 29, 2010

(65) Prior Publication Data

US 2011/0104231 A1    May 5, 2011

Related U.S. Application Data

(63) Continuation of application No. PCT/US2009/003307, filed on Jun. 1, 2009.

(60) Provisional application No. 61/129,003, filed on May 30, 2008.

(51) Int. Cl.
*A61K 9/00*    (2006.01)
*A61K 47/04*   (2006.01)
*A61P 1/02*    (2006.01)
*A61P 19/00*   (2006.01)

(52) U.S. Cl. ........ 424/423; 264/624; 264/45.1; 514/770

(58) Field of Classification Search ........................ None
See application file for complete search history.

(56) References Cited

U.S. PATENT DOCUMENTS

| | | | | |
|---|---|---|---|---|
| 6,323,146 | B1 * | 11/2001 | Pugh et al. | 501/1 |
| 6,993,406 | B1 * | 1/2006 | Cesarano et al. | 700/119 |
| 2007/0213832 | A1 * | 9/2007 | Wen | 623/23.5 |

FOREIGN PATENT DOCUMENTS

| | | |
|---|---|---|
| WO | 8809769 A1 | 12/1988 |
| WO | 2008025122 A1 | 3/2008 |

OTHER PUBLICATIONS

International Search Report and Written Opinion for US Application PCT/US2009/003307 mailed Jan. 14, 2010.

* cited by examiner

*Primary Examiner* — Suzanne Ziska

(57) ABSTRACT

The invention provides a high performance porous bioceramic composite that has a high compression strength resulting from the ability to compression form a bioceramic precursor material and a pore forming agent under a high pressure load prior to sintering and/or removing the pore forming agent. Methods of making and using the same are also provided. Optionally, a biopolymer and/or therapeutic agent may be infused into the pores thereby forming the bioceramic composite.

21 Claims, 9 Drawing Sheets

BIOCERAMIC AND BIOPOLYMER COMPOSITE

CROSS-REFERENCE TO RELATED APPLICATIONS

This application is a continuation of International Application No. PCT/US2009/003307, filed Jun. 1, 2009, which claims the benefit of U.S. Provisional Application Ser. No. 61/129,003, filed May 30, 2008, the entirety of each of which is incorporated by reference.

BACKGROUND

Field of the Invention

The present invention relates generally to bioceramic implants and methods of manufacturing the same for use, either alone or in combination with pharmaceutical agents, as bone substitutes in the fields of orthopedics and dentistry.

Any publications or references discussed herein are presented to describe the background of the invention and to provide additional detail regarding its practice. Nothing herein is to be construed as an admission that the inventors are not entitled to antedate such disclosure by virtue of prior invention.

Orthopedic reconstruction procedures routinely involve the surgical introduction of structural implants that provide for skeletal function, rigid fixation and bone integration. The high stresses incurred by these devices when implanted in structurally loaded sites have historically limited material choices to metallic and select polymeric formulations. While mechanical requirements are achieved, these inert materials do not participate in the orderly remodeling of the skeleton and hence incur the potential for long-term rejection.

Currently, the most common practice for replacing damaged or diseased bone is to use autograft (bone removed from the patient). However, high incidences of donor site morbidity, the necessity of a painful second 'harvesting' surgical procedure, and the absence of large quantities of bone available for grafting compromises patient outcomes. Concerns with allografts (bone taken from a cadaver) and xenografts (bone obtained from animals) include: (1) transmission of disease, (2) difficulty of procurement and processing, (3) uncertain immune response, and (4) premature resorption.

As a consequence of the limitations associated with 'natural' grafts, there is significant advantage for the development of synthetic bone grafts that have the potential to offer important advantages, including: elimination of the risk of disease transmission; reduced occurrence of an adverse immunological response; absence of painful 'harvesting' procedure; relatively low costs; unlimited supply; and the ability to incorporate pharmaceutical agents that accelerate the bone healing process.

However, for synthetic bone grafts to be an effective bone substitute, these materials must possess the appropriate physical structure and mechanical properties. Of particular concern for applications involving high structural loads, is the ability to tolerate physiological conditions without implant failure or degradation.

Mechanical fixation of orthopedic implants can lead to structural failure and the unintentional release of particulate debris. Furthermore, implantable devices may require a degree of geometry adjustment to accommodate the specific constraints of an implant site. Consequently, there are clinical advantages for a high performance bone substitute to be able to withstand shaping, drilling and threading, without fragmentation.

The incorporation of biopolymers into bioceramics has the potential to combine the strength, stiffness and osteoconductivity of calcium-based bioceramics with the toughness and controlled biodegradability of a polymeric phase. Methods of fabrication typically involve the infusion of the biopolymer into the interstitial spaces within a bioceramic network, such as the method described in US 2004/0043051A1.

A variety of techniques exists for the production of a porous bioceramic network; see for example, U.S. Pat. Nos. 3,899,556, 3,929,971, 4,654,314, 4,629,464, 4,737,411, 4,371,484, 5,282,861, 5,766,618, 5,863,984 and International Pat. Nos. WO 95/32008 and WO99/19003. A common technique for producing porous ceramic bodies involves the use of pore forming agents as described in U.S. Pat. Nos. 4,629,464, 4,654,314, 3,899,556 and International Pat. No. WO 95/32008.

While the aforementioned techniques for the production of porous bioceramic components successfully results in open porosity in which a biopolymer may be infiltrated, the overall structural performance of these composite devices is low in the context of structural skeletal loads.

As the repair or replacement of bony voids or defects is site specific, pharmaceutical agents, such as bone growth factors, must be locally delivered via an appropriate carrier. Biodegradable polymers have been used as drug delivery vehicles as they can be implanted directly at the site of repair and their rate of degradation and, hence, rate of drug delivery can be controlled. However, such biodegradable polymers do not possess the mechanical properties suitable for hard tissue replacement. As such, there has been an increased interest in polymeric/ceramic composites, as disclosed for example U.S. Pat. No. 5,766,618 and International Pat. No. WO 99/19003.

It would therefore be advantageous to develop a bioceramic and biopolymer composite that has the required biological and mechanical properties to allow successful performance in high load areas of the skeleton. Such composites should allow for the shaping, drilling and threading of the implant to enable a wide range of implant customization techniques during operative placement and fixation. Furthermore, the biopolymer phase would enable the progressive release of pharmaceutical agents to stimulate and accelerate biological processes underway at the implant site.

SUMMARY OF THE INVENTION

In accordance with an aspect of the present invention there is provided a high performance porous bioceramic that has enhanced tensile and compressive strength due to the ability to compression form the bioceramic precursor and a pore forming agent under high load prior to sintering. Methods of making and using the same are also provided.

In accordance with another aspect of the present invention there is provided a bioceramic that has high strength due to the ability to compression form a bioceramic under high load prior to sintering and bioceramic composite wherein pores in the bioceramic have been filed with a biopolymer and/or a therapeutic.

In accordance with another aspect of the present invention there is provided a porous bioceramic that has high strength due to compression forming the bioceramic under high load in combination with a porogen prior to sintering, wherein sintering removes the porogen leaving a porous high strength bioceramic, which may optionally have the pores filed with a biopolymer and/or therapeutic agent.

In accordance with another aspect of the present invention the porogen substantially retains it's volume during compression forming, such that the porogen does not shrink in response to compression forming, only to expand following release of the compression forming forces and crack the green (i.e. non-sintered) body. For example, a spongy material or compressible material, such as Styrofoam, are not suitable porogens for the present invention. Such porogens simply collapse under the pressure of compression forming and result in only interconnected microscopic pores, whereas the pores of the present invention are both microscopic and macroscopic. The macroscopic pores are in the ranges of, for example, about 10 to about 500 µm, about 50 to about 400 µm, about 100 to about 350 µm, or about 150 to about 300 µm, in diameter. Likewise, porogens that compress significantly under the forming pressure, but expand upon release of the pressure, are unsuitable for the present invention, as the post-forming expansion of the included porogen would crack or fracture the green body. Equally, porogens that do not crack the green body upon release from the compression forming process, but subsequently expand in the subsequent sintering process and damage the compression molded part are unsuitable for the present invention. In addition, gas forming compounds are not suitable porogens, as the formation of gas is not practical under a compression molding process. Exemplary porogens include, but are not limited to, organic particles (e.g., corn or potato starch, wood dust or wood pulp, sugar, ground coffee beans or other ground plant matter, etc.), carbon-based particles (e.g., charcoal, coke, graphite, etc.), petroleum-based particles (e.g., carbon black, paraffin, etc.) and salts (e.g. sodium chloride, magnesium chloride, etc.).

In accordance with still another aspect of the present invention there is provided a high performance bioceramic and biopolymer composite that withstands a wide range of implant customization techniques during operative placement. In yet another exemplary embodiment, the invention provides a bioceramic and/or bioceramic composite having a compression strength of at least about 10 MegaPascal (MPa), at least about 20 MPa, between about 10 and about 100 MPa, between about 20 and about 100 MPa, or between about 20 and about 90 MPa.

In accordance with yet another aspect of the present invention there is provided a high performance bioceramic and biopolymer composite that enables the post-implantation release of pharmaceutical compounds contained in the biopolymer phase.

In accordance with a further aspect of the present invention there is provided a method for producing a porous bioceramic comprising compacting a bioceramic precursor in combination with a compression resistant porogen, sintering the bioceramic/porogen mixture and removing the porogen by either subsequently dissolving the porogen from within the bioceramic or by pyrolysis of the porogen during sintering, wherein the resulting bioceramic may optionally have the pores filled by infusing the bioceramic with a biopolymer and/or a therapeutic agent.

In accordance with a further aspect of the present invention there is provided a method for producing a bioceramic composite comprising mixing a porogen and a bioceramic precursor composition, placing the porogen/bioceramic mixture in a mold, compacting the porogen/bioceramic mixture, releasing the composite from the mold, sintering the bioceramic and optionally infusing the bioceramic with a biopolymer and/or a therapeutic agent.

In accordance with a further aspect of the present invention there is provided a method for producing a bioceramic composite comprising mixing a porogen and a bioceramic precursor composition, placing the porogen/bioceramic mixture in a mold, compacting porogen/bioceramic mixture, sintering the bioceramic, and releasing the composite from the mold and optionally infusing the bioceramic with a biopolymer and/or a therapeutic agent.

Exemplary therapeutic agents include, but are not limited to, members of the BMP protein family, such as osteogenically active forms of OP-1, OP-2, OP-3, BMP-2, BMP-3, BMP-4, BMP-5, BMP-6, BMP-9, BMP-10, BMP-11, BMP-13, BMP-15, GDF-1, GDF-3, GDF-5, GDF-6, GDF-7, and amino acid sequence variants thereof, analgesics and/or antibiotics. See U.S. Patent Pubs. 2008/0014250 and 2009/0048412.

A significant improvement provided by the invention is the production of a synthetic bone replacement/regeneration ceramic that possess the clinically required mechanical properties for high load applications, while maintaining the ability to be fully remodeled by the body.

A high performance bioceramic and biopolymer composite bone substitute, a method of its manufacture and use are provided herein. The bioceramic, which may optionally include a biopolymer and/or therapeutic agent, addresses the limitations of prior techniques to form high performance and/or highly compression resistant implants that retain the benefits of pore formation without a substantial sacrifice in performance and/or compression resistance. The technique involves the initial preparation of a fully sintered bioceramic body prepared with a controlled concentration of interconnected pores that may be subsequently infiltrated with a polymeric species and/or a therapeutic agent.

It has been found that high performance bioceramic and bioceramic composites can be formed based on the use of high compression molding of the bioceramic in the green state, and optionally the resulting pores may subsequently be substantially filled by biopolymer infusion. Furthermore, certain pore forming agents (i.e., porogens) have been identified that can withstand the high compaction pressure (e.g. between about 30 MPa and about 60 MPa) incurred during forming in the green state and that my be subsequently removed from the compacted bioceramic through high temperature sintering to produce a porous structure of high mechanical strength. The subsequent infiltration of the porous bioceramic with a biopolymer produces an implantable device having a mechanical strength sufficient to withstand customization through shaping, drilling and/or threading. Furthermore, a biopolymer may be used as a drug delivery aid for the release of pharmaceutical compounds at the implant site.

The composite may be tailored by varying a) the composition of the bioceramic precursor; b) the composition and/or particle size and/or relative quantity of the porogen; c) the selection of the biopolymer relative to another; and/or d) by the quantity of the porogen added. Likewise, the bioceramic may be primarily hydroxyapatite, tricalcium phosphate, magnesium stabilized calcium phosphate, silicon substituted calcium phosphate or mixtures thereof. The greater the porogen content in the milled powder, generally the higher the level of porosity observed in the sintered ceramic and the higher the fraction of biopolymer that can be incorporated in the final composite. Composites prepared with the inclusion of 0-80 wt % graphite have been successfully prepared and have allowed for the fabrication of composites having a composition ratio of 95/5 to 65/35, bioceramic to biopolymer.

After compaction and sintering of a bioceramic precursor composition and porogen, the porogen is at least partially removed, and in certain examples at least substantially removed, to produce a porous bioceramic structure, which may optionally be infused with a biopolymer and/or therapeutic agent. The porogen may be removed by any suitable method, for example by leaching the porogen in solution or by pyrolysis during sintering of the bioceramic structure.

A high performance bioceramic bone substitute, optionally carrying a biopolymer, and method of making and method of use thereof may overcome one or more of the disadvantages of the prior art and provides one or more of the following advantages:

1. High mechanical strength of the bioceramic phase is attained through high force compression of the green body followed by high temperature sintering;

2. Pore formation (e.g., to enable subsequent biopolymer infiltration) occurs through the use of porogens that withstand the high compressive loads incurred during green body compaction;

3. Pore formation in the bioceramic structure occurs through the high temperature sintering of the bioceramic structure—no additional processing steps are required;

4. Polymeric infiltration occurs at low temperatures and consequently there is no degradation of the mechanical and biological properties of the biopolymer due to processing;

5. The biopolymer may be selected for structural advantages or for the ability to provide controlled release of pharmaceuticals (e.g. BMP) that influence tissue repair and regeneration;

6. The combination of the porous bioceramic and the infiltrated biopolymer enables the bioceramic composite to be readily handled and shaped, for example, by the surgeon, using standard techniques; and/or 7. The bioceramic or composite may be secured into place using standard orthopedic fixation techniques, such as screws threaded through predrilled holes in the implant, without structural damage or the generation of particulate debris.

DETAILED DESCRIPTION OF THE INVENTION

Figure 1:
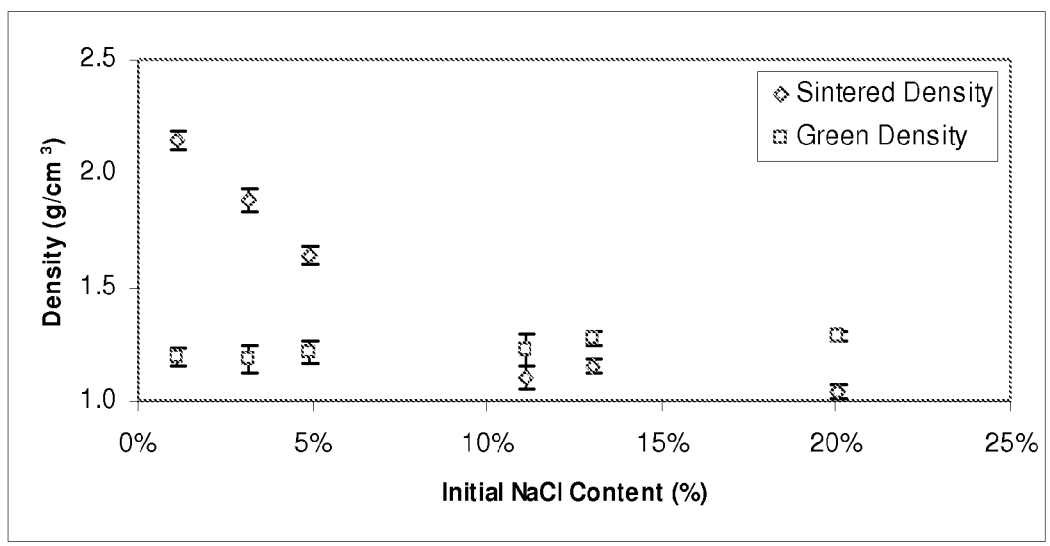
FIG. 1 illustrates the green and sintered densities of bioceramic samples prepared from powders incorporating various amounts of NaCl as the porogen.

For the purposes of promoting an understanding of the principles of the invention, reference will now be made to certain embodiments and specific language will be used to describe the same. It will nevertheless be understood that no limitation of the scope of the invention is thereby intended, such alterations and further modifications in the illustrated device, and such further applications of the principles of the invention as described herein being contemplated as would normally occur to one skilled in the art to which the invention relates.

The uses of the terms "a" and "an" and "the" and similar references in the context of describing the invention (especially in the context of the following claims) are to be construed to cover both the singular and the plural, unless otherwise indicated herein or clearly contradicted by context. For example, the term "a biopolymer" or "at least one biopolymer" may include a plurality of biopolymers, including mixtures thereof. As another example, the term "a pharmaceutical agent" or "at least one pharmaceutical agent" may include a plurality of pharmaceutical agents, including mixtures thereof. As yet another example, the term "a bioceramic precursor composition" or "at least one bioceramic precursor composition" may include a plurality of calcium phosphate based bioceramic precursors, including mixtures thereof. The terms "comprising", "having", "including" are intended to be open-ended and mean that there may be additional elements other than the listed elements.

Recitation of ranges of values herein are merely intended to serve as a shorthand method of referring individually to each separate value falling within the range, unless otherwise indicated herein, and each separate value is incorporated into the specification as if it were individually recited herein.

All methods described herein may be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The bioceramic and/or bioceramic composite described herein may be used in the treatment of a variety of orthopedic and dental disorders, including but not limited to, healing or repairing bone voids, fractures, breaks and any other defects, preventing the collapse of two adjacent vertebrae, spinal or cervical fusion, and combinations thereof.

As used herein, "comprising," "including," "containing," "characterized by," and grammatical equivalents thereof are inclusive or open-ended terms that do not exclude additional, unrecited elements or method steps, but will also be understood to include the more restrictive terms "consisting of" and "consisting essentially of."

As used herein, a "biopolymer" means one or more polymers that are biocompatible.

The invention will now be more particularly described with reference to the following specific examples. It will be understood that these examples are illustrative and not limiting of the embodiments of the invention.

EXAMPLE 1

Example 1

Preparation and Testing of a Bioceramic, Including a Bioceramic Composite

A silicon-substituted mixed-phase calcium phosphate species is precipitated from a reaction mixture of calcium hydroxide and o-phosphoric acid and aged with a silicon source added to the precipitate (see U.S. Pat. No. 6,323,146). The precipitate is dried, crushed and calcined at 900° C. for 1 hour. The crystalline product is then combined with polyethylene glycol, polyvinyl alcohol and a pore forming species and wet milled into a fine powder. The powder is then transferred into a die and pressed uniaxially under ½ ton per cm$^2$ load (or approximately 50 MPa) into various sample shapes, which are then fired for an hour at 1200° C. to sinter the samples and to remove the porogen. The sintered samples with inherent porosity are infiltrated with alternate biopolymers (e.g. polycaprolactone) to produce the bioceramic and biopolymer composite.

Figure 2:
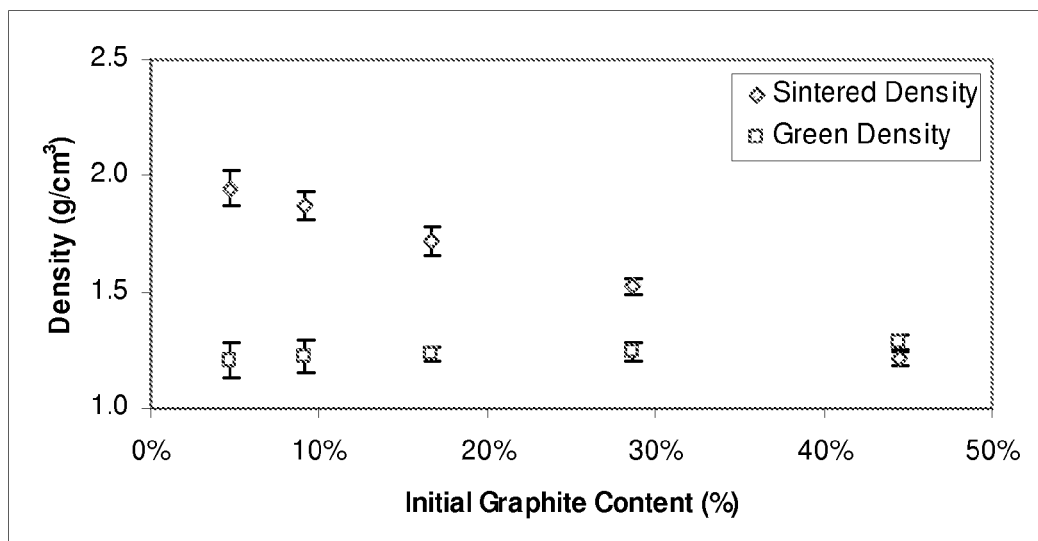
FIG. 2 illustrates the green and sintered densities of bioceramic samples prepared from powders incorporating various amounts of graphite (sieved 150-600 mm) as the porogen.
Figure 3:
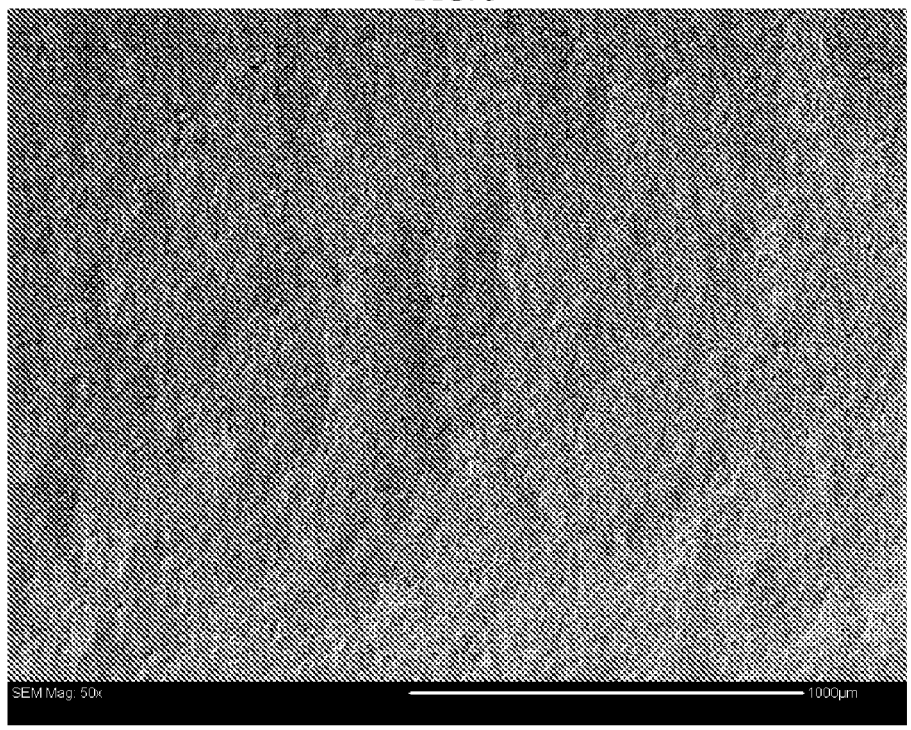
FIG. 3 is a scanning electron microscope (SEM) image of a fracture surface of a a sintered bioceramic sample prepared without any porogen showing no macro porosity (magnification 50×).
Figure 4:
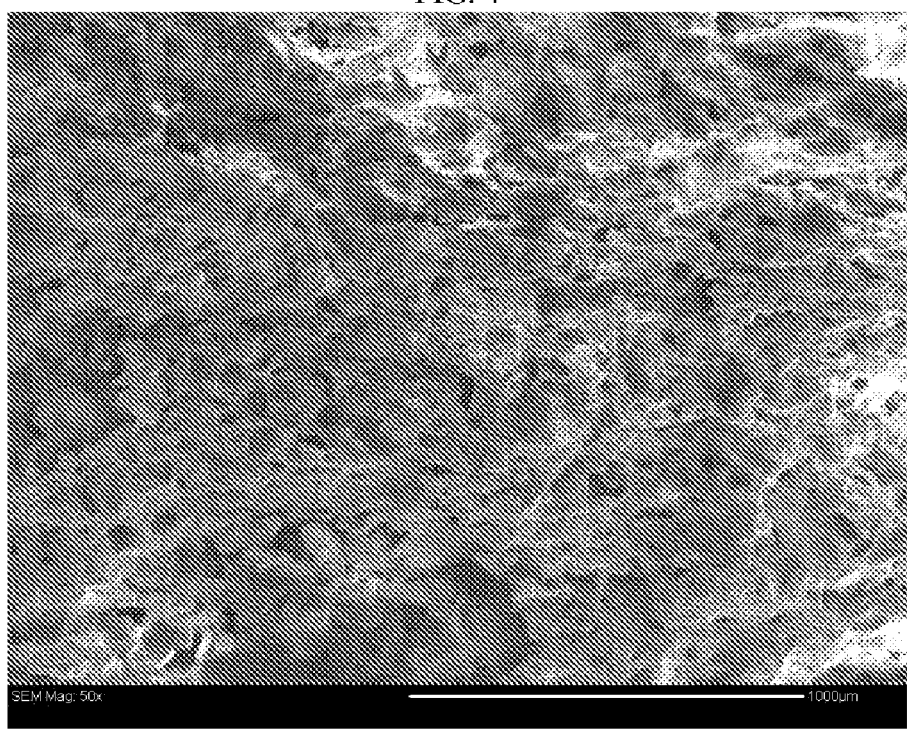
FIG. 4 is a SEM image of a fracture surface of a sample prepared with 44% graphite as the porogen showing the macro porosity arising from the elimination of the porogen (magnification 50×).

Graphite and sodium chloride (NaCl) were examined to determine their suitability as pore forming species in preparing porous sintered calcium phosphate ceramics. The influence of NaCl and graphite on the green and sintered densities of the bioceramic component is shown in FIGS. 1, 2. In samples prepared with either porogen, the level of porosity was found to be highly controllable and related to the quantity, particle size and amount of the incorporated porogen. The samples prepared with sodium chloride exhibited a significantly greater increase in porosity with increases in porogen concentration. Sodium chloride reduces shrinkage; consequently, the void fraction is greater for similar porogen addition levels. In contrast, macro pores formed through the high temperature elimination of graphite were solely a result of graphite removal as sample volume shrinkage was observed to be generally independent of porogen concentration. SEM micrographs of fracture surfaces were taken of sintered bioceramic samples prepared with and without a graphite pore former (FIGS. 3, 4).

Figure 5:
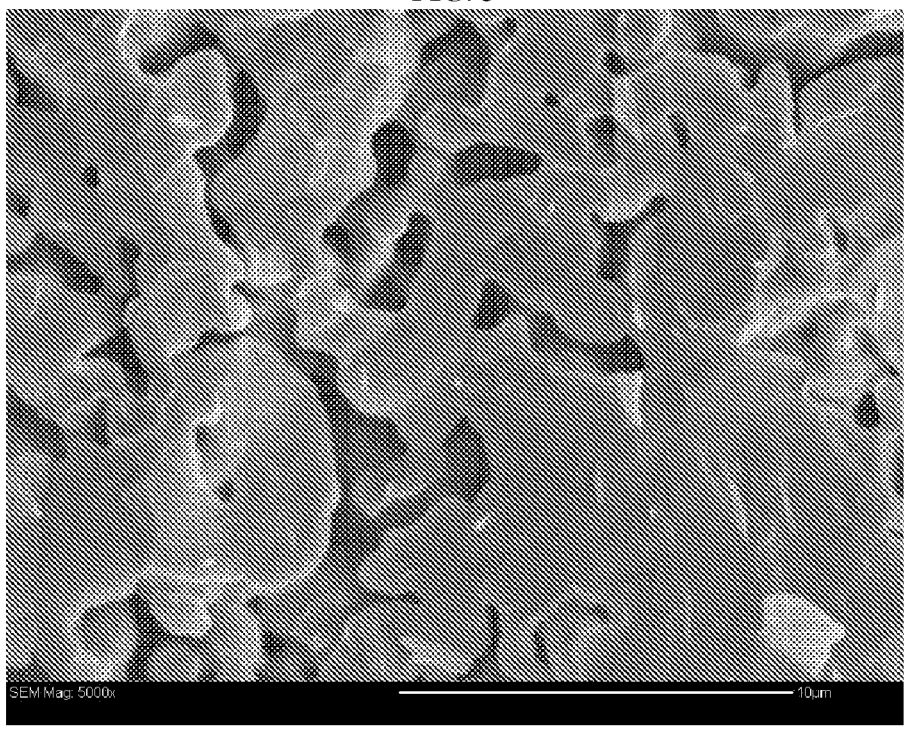
FIG. 5 is a SEM image of a fracture surface of a sintered bioceramic sample prepared without any porogen showing retained micro porosity (magnification 5000×).
Figure 6:
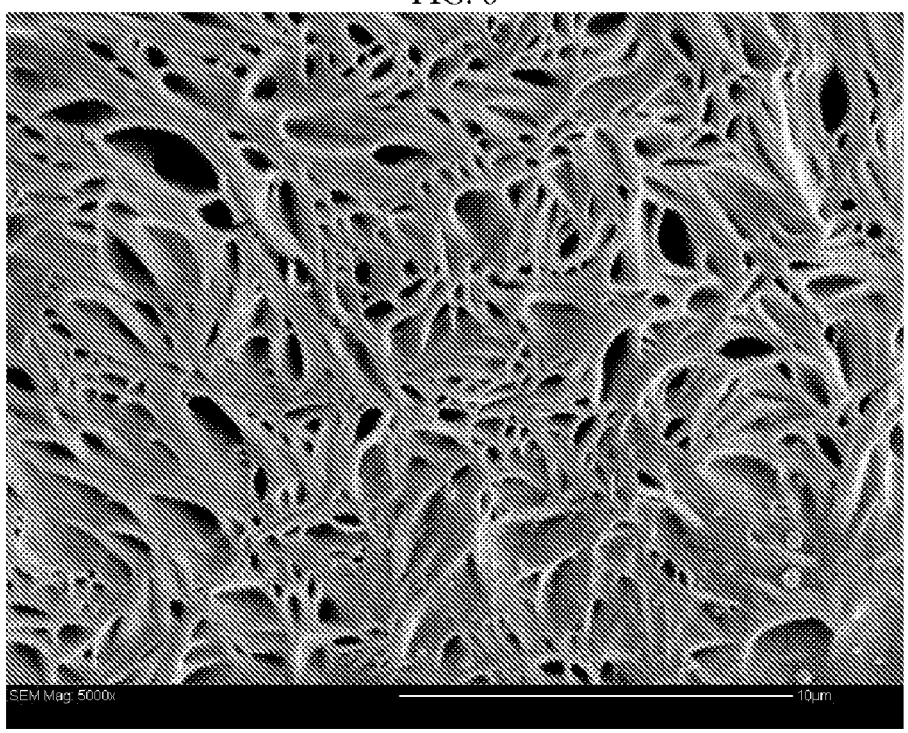
FIG. 6 is a SEM image of a fracture surface of sintered bioceramic sample prepared without any porogen and subsequently infused with polycaprolactone at a ratio of 8/92 PCL/CaP (magnification 5000×).
Figure 7:
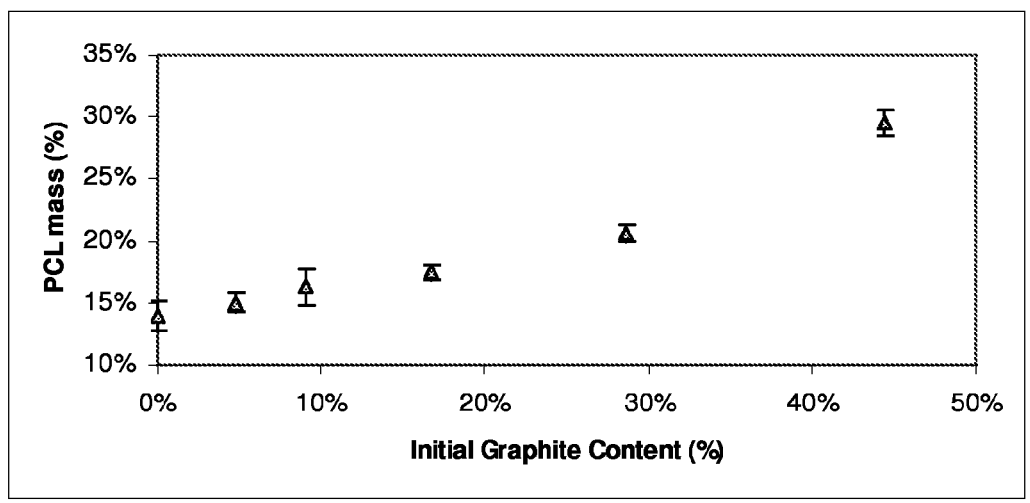
FIG. 7 illustrates the effect of the initial graphite content on the subsequent mass of the biopolymer PCL that can be incorporated in the final composite product.
Figure 8:
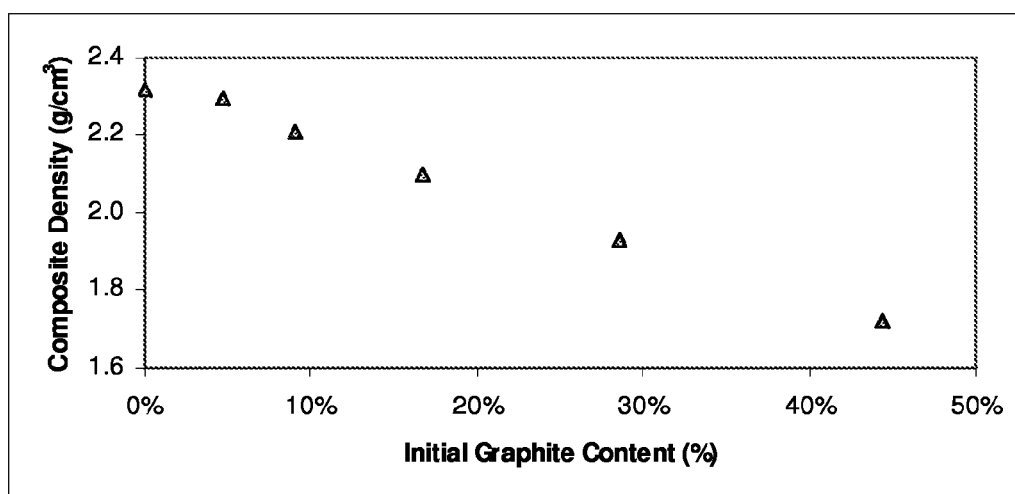
FIG. 8 illustrates the composite density as a function of initial graphite content. The higher the concentration of the less dense PCL in the bioceramic composite, the lower the overall density of the final composite product.
Figure 9:
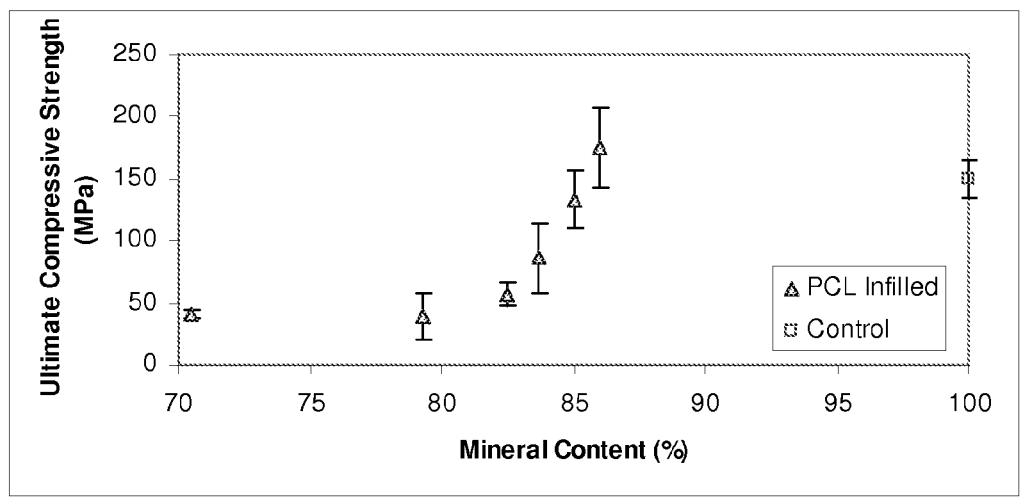
FIG. 9 illustrates the ultimate compressive strength (UCS) of the final composite product as a function of mineral content. The UCS increases with an increase in the mineral content.

Polycaprolactone (PCL), as a representative biopolymer, was successfully infiltrated throughout the porous sintered bioceramics prepared with either pore former, and composites with high mineral content (70-95 wt %) were prepared. SEM micrographs were taken of samples prepared with and without polycaprolactone (FIGS. 5, 6). The mass of PCL in the final composite product was found to be dependent on the initial porogen content (FIG. 7). The graphite pore former is removed during sintering leaving a porosity proportional to its initial concentration. A higher level of porosity allows for a greater mass of PCL to be added into the composite.

Figure 10:
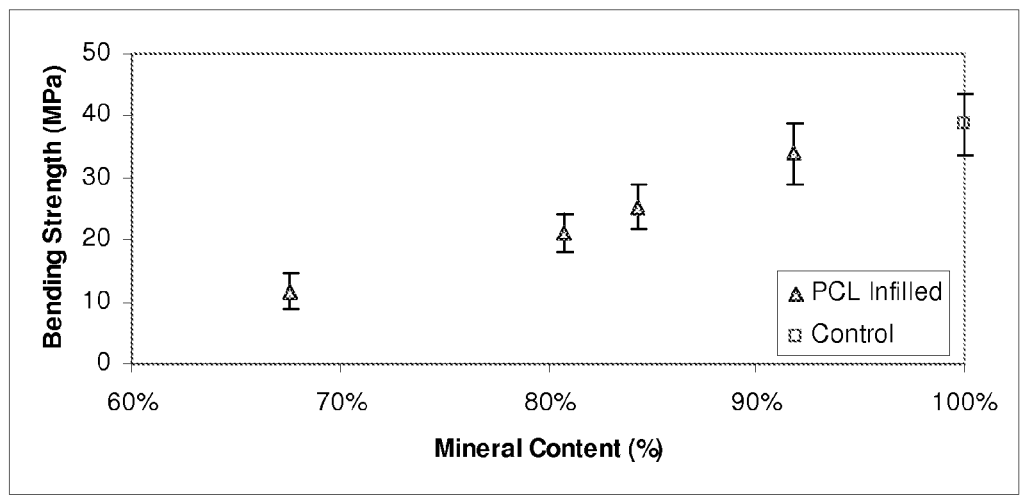
FIG. 10 illustrates the 4-point bending strength as a function of mineral content of the final composite product. The bending strength increases with an increase in the mineral content.

Compressive and 4-point bending strengths of the composites were measured at various polymer to mineral ratios. The strength of the composite was found to increase in both compression and bending with an increase in the composite mineral content (FIG. 10).

Figure 11:
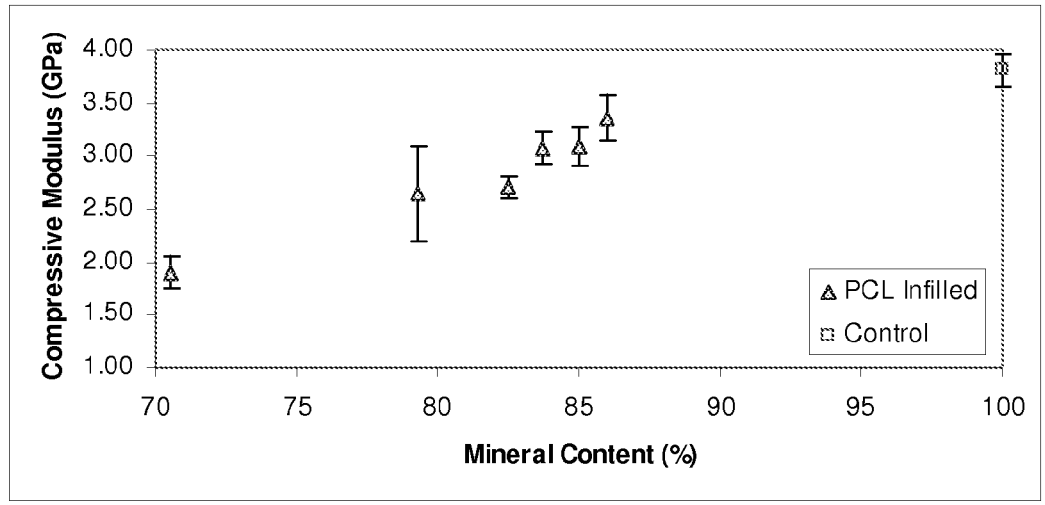
FIG. 11 illustrates the compressive modulus of the final composite product as a function of mineral content. The compressive modulus increases with an increase in the mineral content. Note: This data was generated from an Instron compression test and inherently incorporates the flexure of the test apparatus. Data from ultrasonic Young's Modulus testing indicate compressive modulus of 3.5 to 25 GPa for similar samples.
Figure 12:
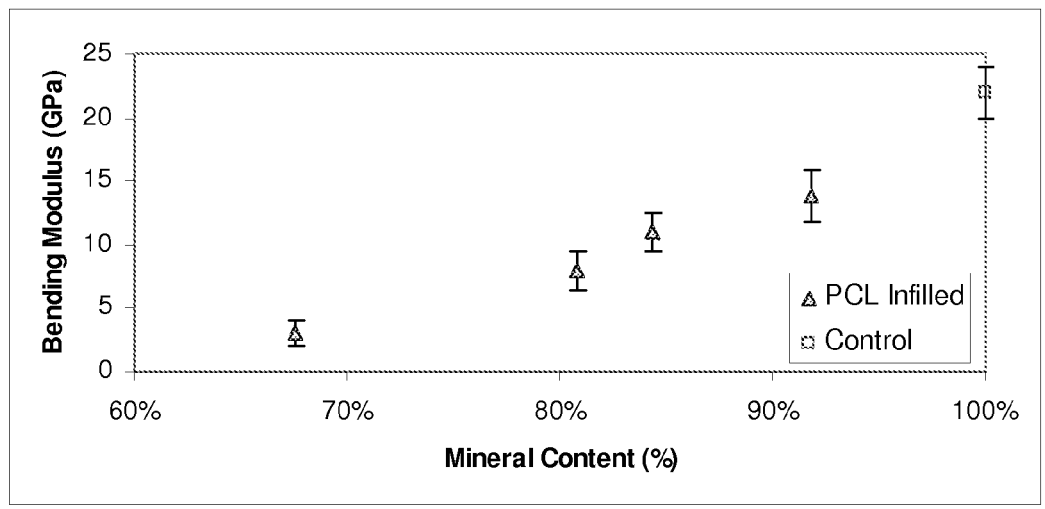
FIG. 12 illustrates the bending modulus of the final composite product as a function of mineral content. The bending modulus increases with an increase in the mineral content. Note: This data was generated from an Instron four point bending test and inherently incorporates the flexure of the test apparatus. Data from ultrasonic Young's Modulus testing indicate bending modulus of 4 to 70 GPa for similar samples.

The compressive and bending moduli were also both found to increase along with an increase in the composite mineral content (FIG. 11, 12).

Figure 13:
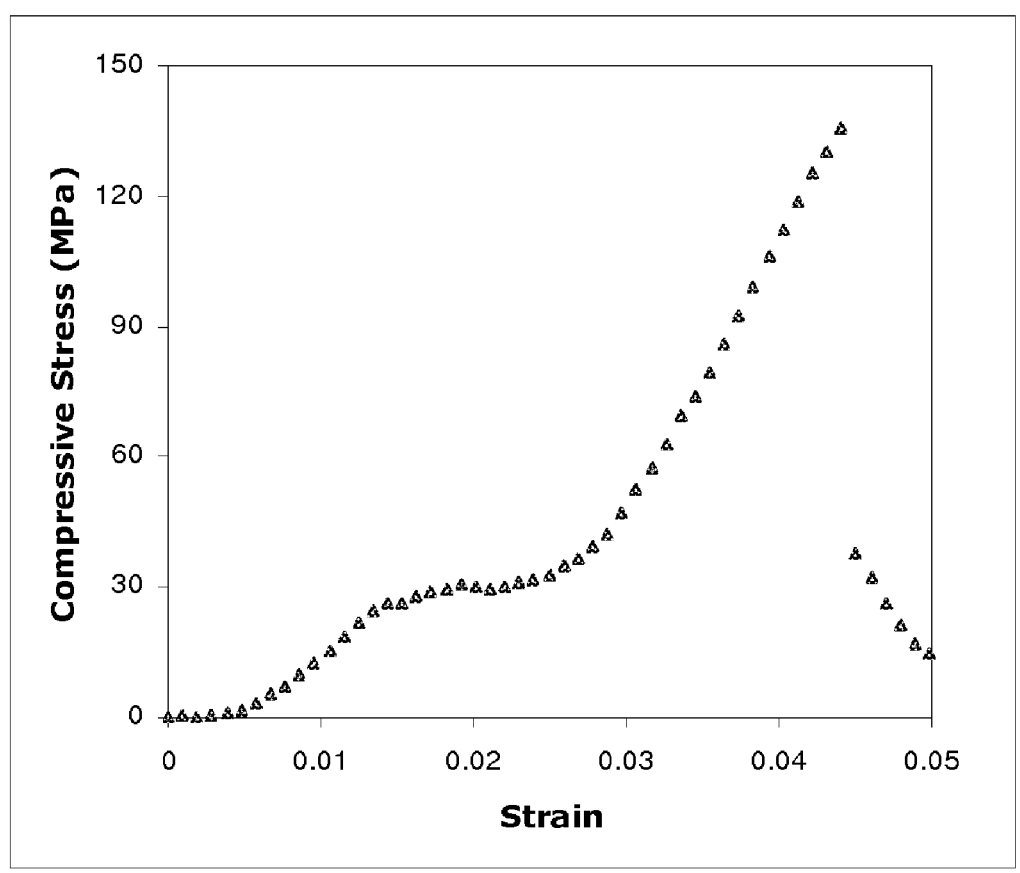
FIG. 13 illustrates a characteristic stress-strain curve for a 15/85 PCL/CaP final composite product under compression (strain rate=0.1 mm/s) Note: This data was generated from an Instron compression test and inherently incorporates the flexure of the test apparatus. Data from ultrasonic Young's Modulus testing indicate 0.008 strain at failure.
Figure 14:
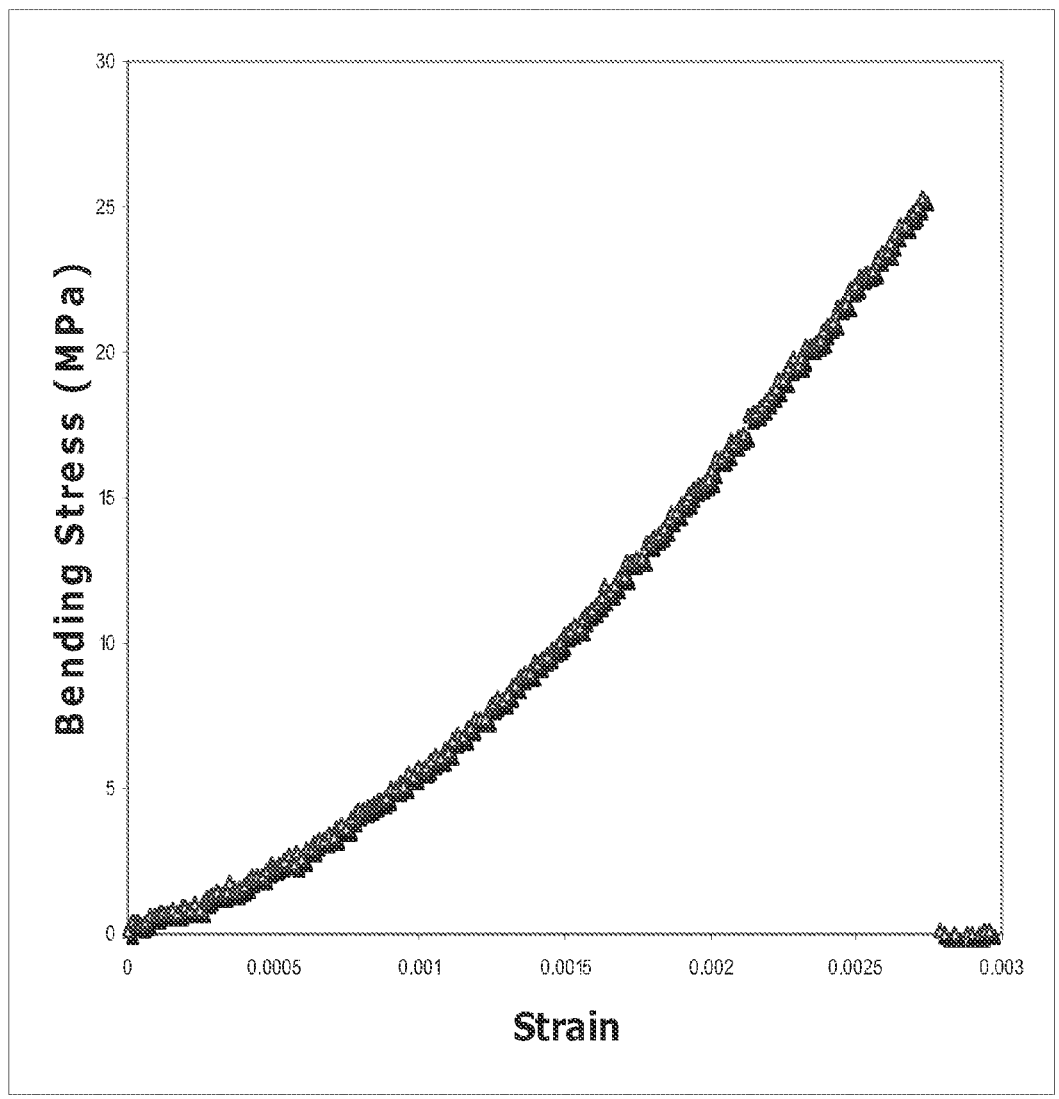
FIG. 14 illustrates a characteristic stress-strain curve for a 15/85 PCL/CaP final composite product in 4-point bending (strain rate=0.15 mm/s) Note: This data was generated from an Instron four point bending test and inherently incorporates the flexure of the test apparatus. Data from ultrasonic Young's Modulus testing indicate 0.002 strain at failure.

The stress-strain curves of 15/85 PCL/CaP composites tested under compression and 4-point bending (FIGS. 13, 14), indicates an initial linear elastic region (strain=0 to 0.015) followed by a plateau of constant stress (strain=0.015 to 0.025). A densification stage follows until ultimate compressive failure.

Figure 15:
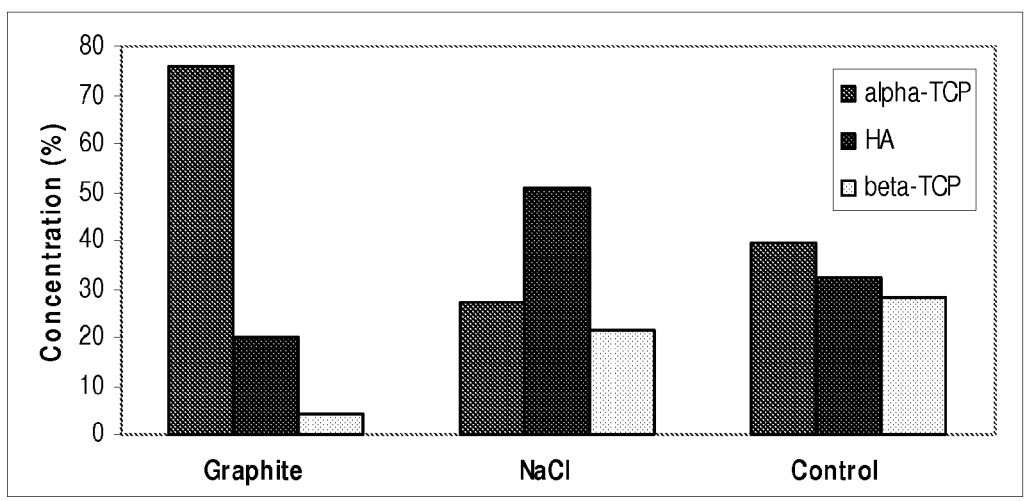
FIG. 15 illustrates Reitfeld refinement estimates of the concentration of each calcium phosphate phase present in the bioceramic after sintering with graphite, NaCl or without a pore former.

The addition of a pore forming agent to the bioceramic powder has an influence on the final concentration of calcium phosphate phases present. The addition of graphite stabilizes the α-TCP phase, whereas the addition of salt promotes the formation of HA (FIG. 15).

The porogens evaluated were: graphite, carbon black, NaCl, MgCl$_2$, wood pulp and PVA.

For the purposes of the present invention, any particulate that is of 10-500 μm, or 75-300 μm, in size can be used as the pore forming agent and incorporated effectively into the wet-milled bioceramic precursor powder, where optionally the pore forming agent may be effectively dissolved or burnt out during sintering.

Figure 16:
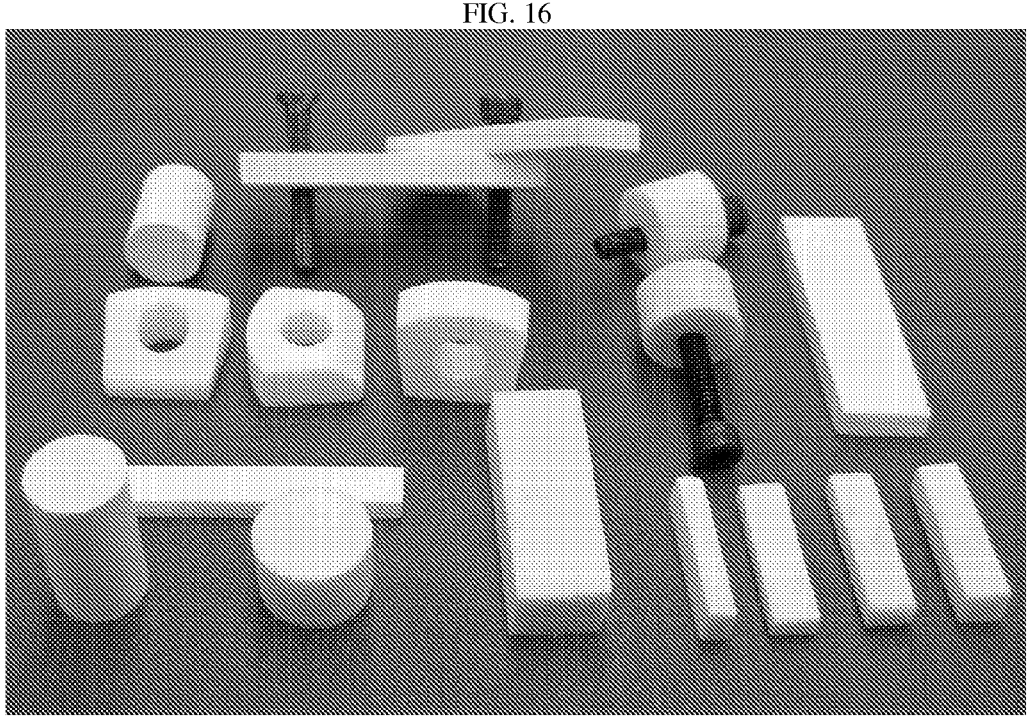
FIG. 16 is a picture showing exemplary devices that can be constructed using the calcium phosphate and biopolymer composite of the invention.

The process of the invention may be adopted to produce orthopedic and dental implants in a variety of shapes and sizes (FIG. 16). These bioceramic composite devices retain high mechanical performance yet also provide for a wide range of implant customization techniques during operative placement and fixation. Furthermore, the biopolymer phase provides for the release of stored pharmaceutical agents at the site of implantation.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all publications cited herein are hereby incorporated by reference in their entirety.

What is claimed is:

1. A method for producing a bioceramic comprising:
   admixing a calcium phosphate powder comprising a silicon-substituted calcium phosphate and a pore forming agent to produce a bioceramic precursor mixture;
   placing the bioceramic precursor mixture in a mold;
   compacting the bioceramic precursor mixture;
   sintering the bioceramic precursor mixture to produce a bioceramic; and
   infusing the bioceramic with a biopolymer to produce a bioceramic composite,
   wherein the bioceramic composite has a modulus between approximately 1.5 GPa and approximately 3.5 GPa, wherein the pore forming agent is graphite, thereby stabilizing the bioceramic composite.

2. The method according to claim 1, wherein the pore forming agent is selected from the group consisting of organic particles, carbon-based particles, petroleum-based particles, salts and combinations thereof.

3. The method according to claim 1, wherein sintering the bioceramic precursor retains substantially interconnected microporosity throughout at least a portion of the bioceramic including exposure on the surface of the bioceramic.

4. The method according to claim 1, wherein the calcium silicon-substituted phosphate powder comprises a mixed-phase silicon-substituted calcium phosphate.

5. The method according to claim 1, wherein sintering the bioceramic precursor mixture comprises heating the bioceramic precursor mixture for about an hour at a temperature between about 1100° C. to about 1300° C.

6. The method according to claim 5, wherein sintering the bioceramic precursor mixture further comprises removing the pore forming agent.

7. The method according to claim 6, further comprising dissolving the pore forming agent from the bioceramic.

8. The method according to claim 1, wherein compacting the bioceramic precursor mixture comprises compacting the bioceramic precursor mixture uniaxially under a pressure of between about 30 MPa and about 60 MPa, optionally 50 MPa.

9. The method according to claim 1, further comprising producing a bioceramic having an ultimate compression strength between approximately 20 MPa and approximately 200 MPa.

10. The method according to claim 1, further comprising infusing the bioceramic composite with a therapeutic agent.

11. A bioceramic or bioceramic composite prepared by the method according to claim 1.

12. A method of treatment of an orthopedic or a dental defect, said method comprising the steps of:
   (a) preparing a region of defect for an implant comprising the bioceramic or bioceramic composite of claim 11;
   (b) placing the implant in the region,
   (c) securing the implant into region.

13. A bioceramic comprising:
   a calcium phosphate based material having macropores between about 50 to about 400 µm;
   micropores between about 0.01 µm to about 5 µm;
   an ultimate compression strength greater than about 20 MPa; and
   a compressive modulus greater than about 1.5 GPa, wherein the bioceramic is infused with a biopolymer to create a bioceramic composite, wherein the bioceramic composite comprises a pore forming agent comprising graphite and wherein the graphite stabilizes the bioceramic composite.

14. The bioceramic of claim 13, wherein the calcium phosphate based material comprises a silicon-substituted calcium phosphate material.

15. The bioceramic of claim 13, wherein the calcium phosphate based material comprises a mixed-phase calcium phosphate material.

16. The bioceramic of claim 13, wherein the biocompatible biopolymer is infused within the macropores and/or micropores.

17. The bioceramic of claim 16, further comprising a therapeutic agent.

18. The method according to claim 1, wherein the bioceramic comprises up to about 80 wt. % of graphite.

19. The method according to claim 1, wherein the ratio of bioceramic to biopolymer is 95/5 to 65/35.

20. The bioceramic of claim 13, wherein the bioceramic comprises up to about 80 wt. % of graphite.

21. The bioceramic of claim 13, wherein the ratio of bioceramic to biopolymer is 95/5 to 65/35.

* * * * *